United States Patent
Omura et al.

(10) Patent No.: US 7,132,447 B2
(45) Date of Patent: Nov. 7, 2006

(54) SUBSTANCE FKI-1083 AND PROCESS FOR PRODUCING THE SAME

(75) Inventors: Satoshi Omura, Tokyo (JP); Kazuro Shiomi, Tokyo (JP); Rokuro Masuma, Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/491,131

(22) PCT Filed: Dec. 11, 2001

(86) PCT No.: PCT/JP01/10843

§ 371 (c)(1),
(2), (4) Date: Sep. 14, 2004

(87) PCT Pub. No.: WO03/050104

PCT Pub. Date: Jun. 19, 2003

(65) Prior Publication Data

US 2005/0032883 A1   Feb. 10, 2005

(51) Int. Cl.
*A61K 31/35* (2006.01)

(52) U.S. Cl. .................. 514/460; 549/417; 504/292; 435/171; 435/254.1; 435/119

(58) Field of Classification Search ............... 549/417; 514/460; 504/292; 435/171, 119, 254.1
See application file for complete search history.

(56) References Cited

U.S. PATENT DOCUMENTS 6,486,197 B1   11/2002   Omura et al.

FOREIGN PATENT DOCUMENTS

WO   WO 99/24439   5/1999

*Primary Examiner*—Amelia A. Owens
(74) *Attorney, Agent, or Firm*—Young & Thompson

(57) ABSTRACT

The present invention is comprised of culturing microorganism having ability to produce FKI-1083 substance represented by the formula:

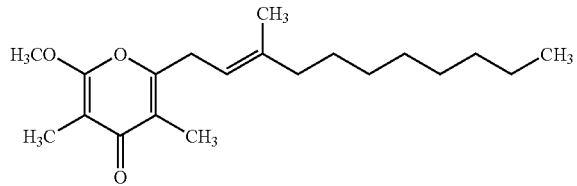

in a medium, accumulating FKI-1083 substance in the cultured medium, and isolating FKI-1083 substance from the cultured mass. The thus obtained FKI-1083 substance has growth inhibitory activities against microorganisms, nematodes and arthropods, and is useful as anthelmintic and insecticide.

4 Claims, No Drawings

SUBSTANCE FKI-1083 AND PROCESS FOR PRODUCING THE SAME

TECHNICAL FIELD

The present invention relates to novel FKI-1083 substance having NADH-fumarate reductase inhibitory activity. More particularly, the present invention relates to a compound of FKI-1083 effective for pharmaceuticals, veterinary medicines and agrichemicals represented by the following formula:

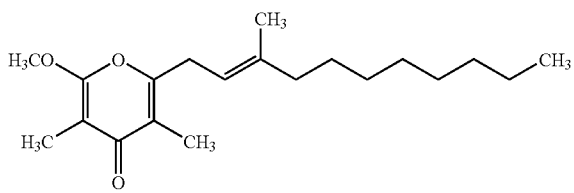

and production thereof.

BACKGROUND ART

Parasitosis has been reducing as the results of improvement in environmental hygiene and progress of anthelmintics, but recently imported parasitosis, zoonotic parasitosis, opportunistic parasitosis and parasitosis derived from raw foods are increasing, as a result various parasitoses become an issue. In livestock farming and agriculture, parasitosis causes great economic burden at present. Among parasitoses, with regard to helminth infection, many compounds such as ivermectin, mebendazole, praziquantel, etc. are used.

However, anthelmintics such as ivermectin, mebendazole and praziquantel are not always satisfactory in view of effectiveness and toxicities, as a result new agents are still demanded.

We have focused to study NADH-fumarate reductase in the electron transport system, one of hopeful targets for anthelmintics, and continued to explore inhibitors against such enzyme from microbial culture products, as a result, we have found FT-0554 substance (nafuredin). The international patent application of this substance was published as the international publication WO99/24439, which was transferred to the U.S. and the application Ser. No. 09/509770 was given.

The microorganism having ability to produce FT-0554 substance (nafuredin) is *Aspergillus niger* FT-0554 belonging to fungi, the strain of which was deposited the International Patent Organism Depository, National Institute of Advanced Industrial Science and Technology, and given a permanent depository No. as FERM BP-6443. Taxonomical properties of the strain are briefly described as follows.

Culturing properties on various agar media such as Czapek-yeast extract agar, malt extract agar, 20% sucrose Czapek-yeast extract agar, potato dextrose agar and Miura's medium, are good growth with velvety and smooth penumbra. Diameter of colony is 40 mm–85 mm. Color tone of the surface of colony is burned umber. Color tone of the reverse of colony is pale yellow or white.

Morphological properties on Czapek-yeast extract agar, malt extract agar, 20% sucrose Czapek-yeast extract agar and potato dextrose agar, containing 50% of seawater (salt content, 3.4%) are good growth with good bearing conidia.

Physiological properties are: optimum growth condition: pH 5–7 at 16–36° C. and in concentration of seawater 50–100%. Growth ranges are pH 3–10, at 12–45° C. and in concentration of seawater 0–100%.

DETAILED DESCRIPTION OF THE INVENTION

We have further continued to study for exploration of novel substances from the cultured microorganisms, and found that the novel compound FKI-1083 substance produced by fungal strain FKI-1083 exhibited inhibitory activity against NADH-fumarate reductase, and completed the present invention.

An object of the present invention is to provide novel substance FKI-1083 substance having inhibitory activity against NADH-fumarate reductase as well as effective in medicament, veterinary drug and agricultural chemicals which is satisfactory in the effectiveness and toxicity.

Namely, an object of the present invention is to provide novel FKI-1083 substance, a compound represented by the following chemical structure:

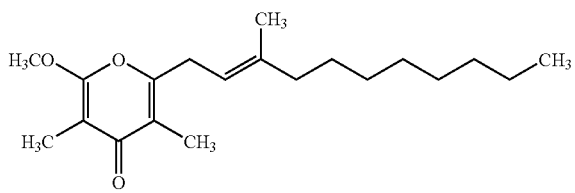

and the novel FKI-1083 substance has growth inhibitory activity against microorganisms, nematodes and arthropods.

Further object of the present invention is to provide a process for production of novel FKI-1083 substance having inhibitory activity of NADH-fumarate reductase.

Namely, further object of the present invention is to provide a process for production of novel FKI-1083 substance comprising culturing a microorganism having ability to produce FKI-1083 substance represented by the following chemical structure:

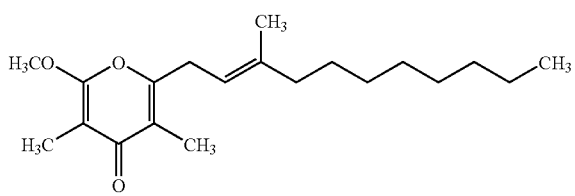

in a medium, accumulating FKI-1083 substance in the cultured medium and isolating FKI-1083 substance from said cultured mass.

Still further object of the present invention is to provide a process for production of FKI-1083 substance wherein the microorganism having ability to produce FKI-1083 substance is *Verticillium* sp. FKI-1083 FERM BP-7804 belonging to fungi.

Further object of the present invention is to provide a microorganism belonging to genus fungi having ability to produce FKI-1083.

Further object of the present invention is to provide a microorganism *Verticillium* sp. FKI-1083 FERM BP-7804.

Further object of the present invention is to provide NADH-fumarate reductase inhibitor comprising FKI-1083 substance represented by the following chemical structure:

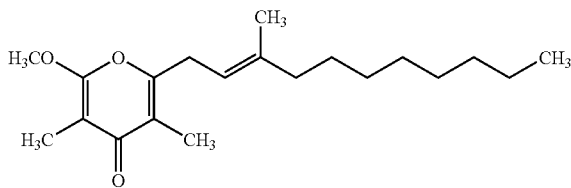

The microorganism having ability to produce novel FKI-1083 substance represented by the formula hereinabove (hereinafter designates as "FKI-1083 substance producing microorganism") is fungus, and can be the microorganism having ability to produce FKI-1083 substance of the present invention without specific limitation. Preferable example of the strain used for production of FKI-1083 substance of the present invention is a fungal strain FKI-1083, which was newly isolated from soil sample of Kagoshima Pref. by the inventors of the present invention. Taxonomical properties of the strain are as follows.

(1) Morphological Properties

The strain showed relatively good growth on potato dextrose agar, potato carrot agar, soil extract agar, cornmeal agar and Miura's medium. Good bearing of conidia was observed on potato carrot agar, soil extract agar, cornmeal agar and Miura's medium. Slightly suppressive bearing of conidia was observed on potato dextrose agar.

Microscopic observation of colonies grown on cornmeal agar shows transparent hyphae with septa, conidiophores standing from the aerial mycelia with branching in some times. The phialide is observed in the middle part or edge of the conidophores. The phialide (17.0–34.0×1.5–2.5 μm) is generated with solely or 2–4 verticillations with slightly swelling in the base and narrowing with the pyramidal shape of edge. Conidiophore with subspherical to broad elliptical shape (2.5–5.0×2.5–3.0 μm) was formed from the edges of the phialide to form viscous globose.

(2) Culture Properties on Various Agar Media

Macroscopic observations of the strain cultured on various agar media at 25° C. for 14 days are shown in Table 1.

TABLE 1

| Medium | Growth condition on medium (diameter of colony) | Color of surface of colony | Color of reverse of colony | Soluble pigment |
|---|---|---|---|---|
| Potato dextrose agar | Good (52–53 mm), Floccose, Bulgy Smooth penumbra | White | Cream - Pale yellowish brown | None |
| Potato carrot agar | Good (57–58 mm), Floccose, Bulgy, Smooth penumbra | White | White - Pale yellowish brown | None |
| Soil extract agar | Good (39–40 mm), Floccose, Bulgy, Smooth penumbra | White | White | Yellow |
| Cornmeal agar | Good (43–46 mm), Floccose - velvety, Smooth penumbra | White | White | None |
| Miura's medium | Good (50–52 mm), Floccose, Smooth penumbra | White | White | None |

(3) Physiological Properties (1) Optimum growth condition

Optimum growth condition of the strain is pH 5–8 at 16–25° C.

(2) Growth range

Growth range of the strain is pH 3–9 at 6–29° C.

(3) Nature for growth condition: aerobic

As a result of comparison with the morphological properties, culture properties and physiological properties of the strain FKI-1083 and known strains, the present strain was identified as a strain belonging to genus *Verticillium*, and was referred to *Verticillium* sp. FKI-1083. The strain was deposited as *Verticillium* sp. FKI-1083 in International Patent Organism Depository, National Institute of Advanced Industrial Science and Technology of AIST Tsukuba Central 6, 1—1, Higashi 1-chome, Tsukuba-shi, Ibaraki-ken, 305-8566 Japan. Date of depository was Nov. 19, 2001 as deposition No. FERM BP-7804.

Production of FKI-1083 substance of the present invention can be performed by culturing FKI-1083 substance producing microorganism belonging to fungi in a medium, isolating from the cultured mass thereof and purifying the same. The strain used in the present invention can be the strain hereinabove described, mutant thereof and every FKI-1083 substance producing microorganism belonging to fungi.

Nutrient sources suitable for production of FKI-1083 substance can be nutrient sources of fungi. For example, commercially available nitrogen sources such as peptone, meat extract, corn steep liquor, cotton seed powder, peanuts powder, soybean meal, yeast extract, NZ-amine, casein hydrolyzate, sodium nitrate, ammonium nitrate and ammonium sulfate, carbohydrates such as glycerin, starch, glucose, galactose and mannose, or carbon sources such as fatty acids, and inorganic salts such as sodium chloride, phosphate, calcium carbonate and magnesium sulfate, alone or in combination thereof.

If necessary, trace metal salts, animal, vegetable and mineral oil as an antifoaming agent can be added. These are preferable substances which can be used by the producing microorganism and useful for production of FKI-1083 substance, and all known materials for culturing fungi can be used. In a mass production of FKI-1083 substance, liquid culture is preferably applied. Culturing temperature can be applied within a range of production of FKI-1083 substance. Culturing condition hereinabove described can be optionally selected depending on properties of FKI-1083 substance producing microorganism.

FKI-1083 substance can be extracted by using water immiscible organic solvent such as chloroform and ethyl acetate from the cultured liquid. In addition to the above extraction, known isolation methods used for purification of fat-soluble substance such as adsorption chromatography, gel filtration chromatography, scratching from thin layer chromatography, centrifugal counter-current chromatography and high performance liquid chromatography can be applied in combination or repeatedly to obtain purified substance.

Physico-chemical properties of FKI-1083 substance of the present invention are as follows.

(1) Nature: colorless oil (2) Molecular weight: 343.2247 (M+Na, high resolution fast atom bombardment mass spectrometry)

(3) Molecular formula: $C_{20}H_{32}O_3$ (4) Ultraviolet absorption spectrum (in methanol): maximum absorption at 204 nm ($\epsilon$=20500), 215 nm (shoulder, $\epsilon$=13720), 250 nm ($\epsilon$=10460)
(5) Infrared absorption spectrum (KBr): maximum absorption at 2927, 2854, 1732, 1670, 1605, 1464, 1408, 1379, 1325, 1250, 1165, 985, 768cm$^{-1}$
(6) $^1$H NMR: chemical shift in deuterated chloroform (ppm) and coupling constant (Hz) are shown in Table 2.
(7) $^{13}$C NMR: chemical shift in deuterated chloroform (ppm) is shown in Table 2.
(8) Solubility in solvent: Soluble in chloroform and ethyl acetate, methanol. Slightly soluble in n-hexane.
(9) Color reaction: Positive for sulfuric acid and iodine reactions.

TABLE 2

| $^{13}$C | $^1$H |
|---|---|
| 183.1 S | |
| 164.5 S | |
| 160.1 S | |
| 140.7 S | |
| 118.7 S | |
| 118.2 d | 5.26 t (1H, J = 7.2) |
| 100.1 s | |
| 56.4 q | 4.00 s (3H) |
| 40.5 t | 2.06 t (2H, J = 7.6) |
| 33.0 t | 1.26 m (2H) |
| 30.8 t | 3.40 d (2H, J = 7.2) |
| 30.5 t | 1.26 m (2H) |
| 30.4 t | 1.26 m (2H) |
| 30.2 t | 1.26 m (2H) |
| 28.8 t | 1.43 m (2H) |
| 23.7 t | 1.28 m (2H) |
| 16.3 q | 1.76 s (3H) |
| 14.4 q | 0.88 t (3H, J = 7.2) |
| 10.0 q | 1.94 s (3H) |
| 7.0 q | 1.80 s (3H) |

In the table, each symbol shows: s, singlet; d, doublet; t, triplet; q, quadplet; m, multiplet; H, number of proton; J, coupling constant (Hz).

As a result of detailed discussion and examination of various physico-chemical properties and spectral data of FKI-1083 substance, chemical structure of FKI-1083 substance was determined to be represented by the following formula.

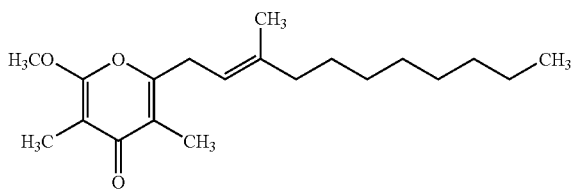

As described hereinabove, various physico-chemical properties of FKI-1083 substance of the present invention are described in detail, and no compound identical with these properties has been reported, consequently FKI-1083 substance of the present invention was determined as a novel substance.

NADH-fumarate reductase inhibitory activity of FKI-1083 substance of the present invention is explained in detail as follows.

Ascaris suum muscle was homogenized in 120 mM sodium phosphate solution (pH 7.0) and centrifuged at 3000×g for 10 minutes to collect the supernatant solution. The solution was further centrifuged at 10000×g for 20 minutes to collect the precipitate. The precipitate was suspended in 120 mM sodium phosphate solution (pH 7.0) to prepare mitochondria fraction. 50% dimethyl sulfoxide solution of FKI-1083 substance 10 µl was added to 96 well microplate. 120 mM sodium phosphate solution (pH 7.0) 80 µl containing 0.35 mM NADH and 7.2 mM disodium fumarate was added thereto and preincubated at 37° C. for 5 minutes in the microplate reader ELX808 (Bio-Tek Industries Inc., the U.S.).

Mitochondria fraction of Ascaris suum muscle 10 µl (0.3 mg protein) was added thereto, incubated at 37° C. for 10 minutes and measured absorption of NADH at 340 nm in every 15 seconds. A gradient of the decrease in absorption at 340 nm was assayed as NADH-fumarate reductase activity. FKI-1083 substance 4.1 nM showed 50% inhibition of NADH-fumarate reductase activity. Consequently, FKI-1083 substance can be expected as a composition for treatment or prevention of helminthiasis.

Minimum inhibitory concentration (MIC) of FKI-1083 substance of the present invention against various microorganisms on nutrient agar medium by agar plate dilution method is shown in Table 3.

TABLE 3

| Test microorganism | MIC (µg/ml) |
|---|---|
| Staphylococcus aureus ATCC6538p | 6.25 |
| Bacillus subtilis ATCC6633 | 6.25 |
| Micrococcus luteus ATCC9341 | 6.25 |
| Mycobacterium smegmatis ATCC607 | 12.5 |
| Escherichia coli NIHJ | >100 |
| Escherichia coli NIHJ JC-2 (IF012734) | >100 |
| Pseudomonas aeruginosa IF03080 | >100 |
| Xanthomonas campestris pv. oryzae KB88 | >100 |
| Candida albicans KF1 | >100 |
| Saccharomyces cerevisiae KF26 | >100 |
| Aspergillus niger ATCC6275 | >100 |
| Mucor racemosus IF04581 | >100 |

As obvious from Table 3 hereinabove, FKI-1083 substance of the present invention exhibited inhibitory activity against various microorganisms.

Next, nematocidal activity and anthropodicidal activity of FKI-1083 substance of the present invention is explained in detail hereinbelow.

Methanol solution of FKI-1083 substance of the present invention was added to a 96 well plate (Corning Inc., the U.S.). Methanol was removed in vacuo. A test medium (lecithin 0.01%, sodium hydrogen carbonate 7.5 mM, potassium chloride 7.5 mM, calcium chloride dihydrate 7.5 mM, and magnesium sulfate heptahydrate 7.5 mM) 250 µl was added thereto and shaken for 15 minutes.

Approximately 10 Caenorhabditis elegans cultured on the agar medium for nematode growth [a medium in which E. coli was cultured on a medium consisting of bactoagar (DIFCO Inc., the U.S.) 1.7%, bactopeptone (DIFCO Inc., the U.S.) 0.5%, yeast extract (DIFCO Inc., the U.S.) 1.0%, sodium chloride 0.3%, cholesterol 0.0005%, calcium chloride 0.007%, magnesium sulfate 0.03%, dipotassium hydrogen phosphate 0.34%, and potassium dihydrogen phosphate 0.11%] were added thereto. Separately, a buffer solution 50 µl containing several numbers of nauplius larvae of Artemia salina hatched in the buffer (Tris 0.24%, sodium chloride 2.57%, magnesium chloride 0.47%, potassium chloride 0.07%, sodium carbonate 0.02%, magnesium sulfate 0.64% and calcium chloride 0.11%, pH 7.1) was added.

Conditions of these nematode and arthropod were observed under microscope. Movement of *Caenorhabditis elegans* and *Artemia salina* was inhibited at the concentration of 20 μg/ml and 2 μg/ml, respectively. Consequently, FKI-1083 substance of the present invention is useful as anthelmintic and insecticide.

BEST MODE FOR CARRYING OUT THE INVENTION

The present invention is explained with an example but is not construed as limiting within the example.

Each one of loopful strain of *Verticillium* sp. FKI-1083 FERM BP-7804 cultured on the agar slant medium was inoculated into a 500 ml Erlenmeyer flask containing 100 ml of liquid medium (pH 5.7) consisting of glucose 2.0%, polypeptone (Nihon Pharmaceutical Co., Japan) 0.5%, yeast extract (Oriental Yeast Co., Japan) 0.2%, agar 0.1%, potassium dihydrogen phosphate 0.1%, magnesium sulfate heptahydrate 0.05% and water, and shake cultured at 27° C. for 3 days. Each one milliliter of this seed culture liquid was inoculated into each one of 20 flasks of 500 ml Erlenmeyer flask containing each 100 ml of liquid medium (pH 6.0) consisting of potato dextrose broth (DIFCO, the U.S.) 2.4%, malt extract (DIFCO, the U.S.) 1.5%, magnesium phosphate octahydrate 0.5%, agar 0.1% and water, and shake cultured at 27° C. for 7 days.

Cultured liquid was centrifuged. The obtained mycelia were extracted with methanol, concentrated in vacuo to remove methanol, and extracted the residue with ethyl acetate to obtain crude substance I, 1.21 g. The crude substance I was charged on a column of silica gel (Art. 7734, Merck Co. the U.S.) packed with hexane-ethyl acetate (10:1), washed the column with the hexane-ethyl acetate (3:1) and eluted with hexane-ethyl acetate (1:1). The eluate was concentrated in vacuo to obtain crude substance II, 81.0 mg. The crude substance II was charged on a column of silica gel (Art. 7734, Merck Co. the U.S.) packed with hexane-ethyl acetate (2:1), and eluted with hexane-ethyl acetate (2:1). The eluate was concentrated in vacuo to obtain FKI-1083 substance, colorless oil, 61.1 mg.

INDUSTRIAL APPLICABILITY

As explained hereinabove, FKI-1083 substance, which is produced and obtained by culturing the microorganism having ability to produce FKI-1083 substance in a medium, accumulating FKI-1083 substance in the medium, and isolating FKI-1083 substance from the cultured mass, has growth inhibitory activities against microorganisms, nematode and arthropod, and is expected as useful substance for medicaments, veterinary drugs and agricultural chemicals.

What is claimed is:

1. A compound represented by the formula:

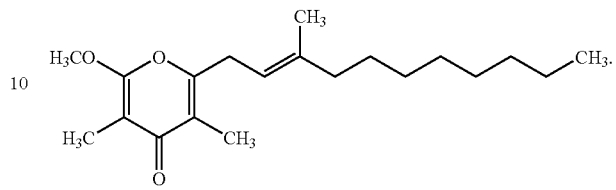

2. A process for production of FKI-1083 substance comprising culturing a microorganism *Verticillium* sp. FKI-1083 FERM BP-7804 having ability to produce said FKI-1083 substance represented by the formula:

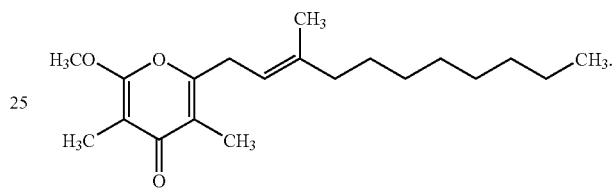

in a medium, accumulating FKI-1083 substance in a cultured mass, and isolating FKI-1083 substance from the cultured mass.

3. A microorganism having the ability to produce the compound according to claim 1, wherein the microorganism is *Verticillium* sp. FKI-1083.

4. A composition comprising FKI-1083 substance represented by the formula:

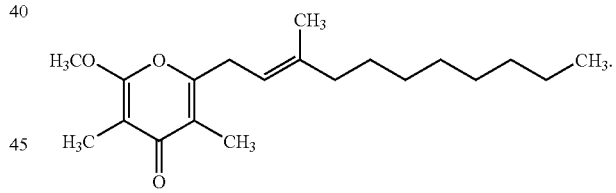

* * * * *